US007473825B2

(12) United States Patent
Takaiwa et al.

(10) Patent No.: US 7,473,825 B2
(45) Date of Patent: Jan. 6, 2009

(54) METHOD OF ACCUMULATING FOREIGN GENE PRODUCT IN PLANT SEED AT HIGH LEVEL

(75) Inventors: Fumio Takaiwa, Tsuchiura (JP); Yoshifumi Tada, Tsukuba (JP)

(73) Assignees: National Institute of Agrobiological Sciences, Ibaraki (JP); National Agriculture and Bio-Oriented Research Organization, Ibaraki (JP)

( * ) Notice: Subject to any disclaimer, the term of this patent is extended or adjusted under 35 U.S.C. 154(b) by 0 days.

(21) Appl. No.: 10/344,964

(22) PCT Filed: Aug. 17, 2001

(86) PCT No.: PCT/JP01/07087

§ 371 (c)(1), (2), (4) Date: May 28, 2003

(87) PCT Pub. No.: WO02/16604

PCT Pub. Date: Feb. 28, 2002

(65) Prior Publication Data

US 2004/0031075 A1 Feb. 12, 2004

(30) Foreign Application Priority Data

Aug. 22, 2000 (JP) ............................. 2000-251606

(51) Int. Cl.
C12N 15/82 (2006.01)
C12N 5/04 (2006.01)
A01H 5/00 (2006.01)

(52) U.S. Cl. .................... 800/320.1; 800/278; 800/290; 800/260; 800/298; 435/419

(58) Field of Classification Search ................. 800/278, 800/298, 287, 290; 435/320.1, 419, 468
See application file for complete search history.

(56) References Cited

U.S. PATENT DOCUMENTS

| 6,211,436 B1 | 4/2001 | Kossmann et al. | |
| 6,235,976 B1 * | 5/2001 | Mueller ...................... | 800/312 |
| 2004/0111766 A1 * | 6/2004 | Huang et al. ................. | 800/288 |
| 2005/0204418 A1 * | 9/2005 | Jung et al. ................... | 800/278 |

FOREIGN PATENT DOCUMENTS

| EP | 0571741 A2 | 12/1993 |
| JP | 7-213185 | 8/1995 |
| JP | 2000-504937 A1 | 4/2000 |
| WO | WO 89/03887 | 5/1989 |
| WO | WO 94/20628 A2 | 9/1994 |
| WO | 97/45545 A1 | 12/1997 |
| WO | 98/27212 A1 | 6/1998 |
| WO | WO 00/08161 A1 | 2/2000 |
| WO | 00/28008 A1 | 5/2000 |

OTHER PUBLICATIONS

Kermode, et al (1995, Planta 197(3):501-513).*
Katsube et al (1999, Plant Physiology 120:1063-1073).*
Takaiwa et al (1991, Plant Molecular Biology 17:875-885).*
Iida et al (1993, Theor. Appl. Genet. 97:374-378).*
Iida et al (1997, Theor. Appl. Genet. 94:177-183).*
Mills et al (2004, Critical Reviews in Food Science and Nutrition 44(5):379-407).*
Momma et al (1999, Biosci, Biotechnol. Biochem. 63(2):314-318).*
Takaiwa et al., 1991, Plant Mol. Biol. 17:875-885.*
Benfey et al (1990, Science 250:959-966).*
Benfey et al (1989, EMBO J, 8(8):2195-2202.*
Izawa et al (1993, J. Mol. Biol. 230 :1131-1144).*
Hao, et al (1998, The J. of Biological Chemistry 273 (41): 26857-26861).*
Takaiwa et al., "Sequence of Three Members and Expression of a New Major Subfamily of Glutelin Genes from Rice," *Plant. Mol. Biol.* 17(4):875-885 (1991).
GenBank Accession No. X54314 (Nov. 20, 1991).
Katsube et al., "Accumulation of Soybean Glycinin and Its Assembly with the Glutelins in Rice," *Plant Physiology* 120:1063-1073 (1999).
Takaiwa et al., "Characterization of Common cis-Regulatory Elements Responsible for the Endosperm-Specific Expression of Members of the Rice Glutelin Multigene Family," *Plant Molecular Biology* 30:1207-1221 (1996).
Washida et al., "Identification of cis-Regulatory Elements Required for Endosperm Expression of the Rice Storage Protein Glutelin Gene GluB-1," *Plant Molecular Biology* 40:1-12 (1999).
Wu et al., "Promoters of Rice Seed Storage Protein Gene Direct Endosperm-Specific Gene Expression in Transgenic Rice," *Plant Cell Physiol.* 39(8):885-889 (1998).
Wu et al., "The GCN4 Motif in a Rice Glutelin Gene is Essential for Endosperm-Specific Gene Expression and is Activated by Opaque-2 in Transgenic Rice Plants," *The Plant Journal* 14(6):673-683 (1998).
Goosens et al., "Co-Introduction of an Antisense Gene for an Endogenous Seed Storage Protein Can Increase Expression of a Transgene in *Arabidopsis thaliana* Seeds," *FEBS Letters* 456:160-164 (1999).
Iida et al., "Mutants Lacking Glutelin Subunits in Rice: Mapping and Combination of Mutated Glutelin Genes," *Theor. Appl. Genet.* 94:177-183 (1997).
Kohno-Murase et al., "Improvement in the Quality of Seed Storage Protein by Transformation of *Brassica napus* with an Antisense Gene for Cruciferin," *Theor. Appl. Genet.* 91:627-631 (1995).
Momma et al., "Quality and Safety Evaluation of Genetically Engineered Rice with Soybean Glycinin: Analyses of the Grain Composition and Digestibility of Glycinin in Transgenic Rice," *Biosci. Biotechnol. Biochem.* 63:314-318 (1999).
Tada et al., "Foreign Gene Products Can Be Enhanced by Introduction Into Low Storage Protein Mutants," *Plant Biotechnol. J.* 1:411-422 (2003).

(Continued)

*Primary Examiner*—Stuart F. Baum
(74) *Attorney, Agent, or Firm*—Nixon Peabody LLP

(57) ABSTRACT

The present inventors succeeded in developing a vector that expresses high levels of a foreign gene in plant seeds by utilizing a 5'-untranslated region of a gene encoding a seed storage protein. The inventors also succeeded in accumulating high levels of a foreign gene product in plant seeds by utilizing a seed storage protein defective mutant as a target for foreign gene transfer.

9 Claims, 4 Drawing Sheets

OTHER PUBLICATIONS

Tada et al., "Reduction of 14-16 kDa Allergenic Proteins in Transgenic Rice Plants by Antisense Gene," *FEBS Letters* 391:341-345 (1996).

Takaiwa et al., "High Level Accumulation of Soybean Glycinin in Vacuole-Derived Protein Bodies in the Endosperm Tissue of Transgenic Tobacco Seed," *Plant Sci.* 111:39-49 (1995).

* cited by examiner

A

B

| Transformant | Expression level | Protein |
|---|---|---|
| N | 1.43 | 1.40 |
| ATG 10 | 6.56 | 1.62 |
| Glycinin (11-5) | 1.00 | 1.00 |

| Name | Protein |
|---|---|
| LGC×11-5 | 1.7 |
| α123×1-5 | 1.4 |
|  |  |
| Glycinin (11-5) | 1 |

METHOD OF ACCUMULATING FOREIGN GENE PRODUCT IN PLANT SEED AT HIGH LEVEL

This application is a national stage application under 35 U.S.C. § 371 of PCT/JP01/07087, filed Aug. 17, 2001, which claims the priority benefit of Japanese Application Serial No. 2000/251606, filed Aug. 22, 2000.

TECHNICAL FIELD

The present invention relates to a method for accumulating high levels of a foreign gene product in plant seeds.

BACKGROUND ART

Seed storage proteins are conventionally classified into four groups of proteins, according to their solubility, i.e., glutelin, globulin, prolamin, and albumin. Rice is different from other grains, such as wheat and maize, in that glutelin is the major seed storage protein, accounting for about 70 to 80% of the seed storage proteins. The glutelin gene group comprises about 10 genes per one haploid genome, and the genes are divided into two subfamilies, GluA and GluB, which show a homology of 60 to 65% at the amino acid sequence level within the coding region. Each subfamily comprises about 5 genes that have a homology of 80% or higher at the amino acid sequence level. A glutelin gene is specifically expressed and accumulated in the endosperm. The tissue specificity of glutelin expression is considerably strictly regulated, and glutelins are not expressed in other tissues, such as leaf and root. The expression of the glutelin gene group, with the exception of GluA-3, is generally coordinated; their mRNA levels show the following pattern: emerging 5 days after flowering (day 5), reaching maximum at around day 15, and decreasing thereafter. The GluB-1 gene has the strongest promoter activity in the glutelin gene group.

Rice mutants with decreased amount of accumulated glutelin, i.e., the major seed storage protein, have been isolated. For example, Iida et al. isolated recessive mutants that lack either one of the acidic subunits of glutelin, α1, α2, or α3, from a rice breed Koshihikari that was irradiated with γ-ray. The phenotypes are respectively regulated by a single recessive gene (i.e., glu1, glu2, or glu3). A mutant strain (α123) that lacks all of α1, α2, and α3 has been also obtained by crossing the above three mutants (Iida, S. et al., Theor. Appl. Genet. 94: 177-183 (1997)).

LGC-1 (low glutelin content-1) is a mutant selected from Nihonmasari treated with EMS, and has a phenotype with a significantly reduced level of glutelin (Iida, S. et al., Theor. Appl. Genet. 87: 374-378 (1993)). LGC-1 is further characterized by increased levels of prolamin and globulin. LGC-1 is dominated by a single dominant gene. By mapping the defective genes in LGC-1 and the mutants defective of α1, α2, and α3, it was revealed that the mutated protein gene (lgc-1) in LGC-1 and the mutated glutelin gene (glu1) in the mutant lacking α1 are localized on the same locus. The results of Southern hybridization using the glutelin (GluB) gene as a probe suggested that LGC-1 contained a mutation in the GluB gene or in the proximity thereof. According to the results of Northern blot analysis, comparing the expression level of the GluB gene in the endosperm after about 16 days from head spout in LGC-1 and its original breed, Nihonmasari, it was revealed that GluB expression is markedly decreased in LGC-1.

In soybean, glycinin is known as a seed storage protein. Glycinin is produced as a precursor polypeptide of a size of about 60 kDa wherein a signal peptide, an acidic polypeptide, and a basic polypeptide are bound together; the signal peptide is cleaved afterwards. Thereafter, a subunit is formed wherein two kinds of polypeptides that result from a cleavage at the Asn-Gly site—i.e., the specific acidic polypeptide (A) and basic polypeptide (B)—are polymerized through disulfide bonds. Six of these subunits are assembled to form a hexamer, and are stored in the protein body (PB) The hexamer is also called "11S seed storage protein", due to its sedimentation coefficient (11S). Glycinin subunits are classified into group I and group II based on the primary structure of their cDNAs and their amino acid sequence homology. To date, subunits A1aB1b, A1bB2, and A2B1a of group I, and subunits A3B4, and A5A4B3 of group II are known. Six of these subunits are known to be almost randomly combined in soybean glycinin. Furthermore, a peptide derived from the A1aB1b subunit of soybean glycinin has been reported to have the ability to bind to bile acid (Shio Makino, The Food Industry 39(24): 77-87 (1996)), which suggests that the ability of soybean proteins to decrease the cholesterol level in blood is dependent on the A1aB1b subunit.

DISCLOSURE OF THE INVENTION

The present inventors focused on the beneficial physiological functions of soybean glycinin, such as the cholesterol decreasing effect described above, and have already succeeded in generating rice wherein the storage protein composition in seeds has been altered by expressing the A1aB1b gene in the endosperm of the rice seeds (Japanese Patent No. 3030339). However, for a desired effect of physiological function to arise from eating the rice, higher levels of expression are necessary. Accordingly, techniques that enable accumulation of higher levels of foreign gene product in rice need to be developed and utilized. The present invention was conducted by taking such requirement into account, and its objective is to provide a method for accumulating high levels of foreign gene product in plant seeds.

In order to achieve the above objective, the present inventors tried to improve the promoter for expressing high levels of a foreign gene in plant seeds. By examining the promoter region of the rice seed storage protein glutelin GluB-1 gene, conventional vectors used for expressing glycinin gene were revealed to incompletely contain the 5'-untranslated region of the glutelin gene. The present inventors focused on the 5'-untranslated region of the glutelin gene, the importance of which has not yet been recognized, and examined the whether the insertion of the 5'-untranslated region into expression vectors would improve the accumulation level of mRNA. The results showed no improvement in the expression level as compared to the conventional glycinin gene transductant associated with the insertion of an enhancer sequence of a tobacco photosynthesis gene between the GluB-1 gene promoter and the glycinin gene (A1aB1b) (pSaDb). However, insertion of the complete 5'-untranslated region of the glutelin (ATG) dramatically increased the accumulation levels of both mRNA and protein.

Previous studies never considered the maximal capacity of gene expression (transcription and translation) in expressing a foreign gene in plants. Therefore, introduction of a foreign gene was attempted only into plant varieties that were ordinarily used for experiments. The present inventors focused on the "maximal capacity" of plants, and presumed that foreign gene products might accumulate at higher levels when mutants defective in a particular protein were used. Accordingly, the inventors attempted to express and accumulate a foreign gene utilizing mutant plants.

Several mutants that lack major storage protein, such as LGC-1 and α123, are known for rice. The present inventors predicted that the amount of free amino acids available for protein translation in such seed storage protein defective mutants is larger than in normal plants, since the free amino acids are not utilized for the biosynthesis of the normally accumulated storage protein. Moreover, the present inventors considered that use of the glutelin promoter in LCG-1 might enable higher levels of foreign gene expression, since the glutelin gene expression is suppressed in LGC-1 and thus transcription factors that are originally used for the expression of glutelin may be utilized for the foreign gene expression. Thus, the present inventors crossed LGC-1 or α123 with 11-5, a glycinin transductant, to introduce the glycinin gene into such mutant, and examined the levels of accumulated glycinin in their seeds. As a result, they found out that the amount of accumulated glycinin protein dramatically increased in both strains of LGCx11-5 and α123x11-5 as compared with 11-5.

Thus, the present inventors succeeded in developing a vector that expresses high levels of a foreign gene in plant seeds by utilizing the 5'-untranslated region of a gene encoding a seed storage protein. They also succeeded in accumulating high levels of a foreign gene product in plant seeds by using a seed storage protein defective mutant as a target for gene transfer, and finally accomplished the present invention.

More specifically, the present invention provides:

(1) a method for accumulating foreign gene product in plant seeds, comprising the steps of: introducing a foreign gene into a plant that is defective in endogenous seed storage protein, and expressing the foreign gene in the plant;

(2) the method according to (1), wherein the foreign gene is introduced using a vector that comprises the foreign gene operatively connected downstream of a promoter which ensures the expression of the foreign gene in plant seeds;

(3) the method according to (1), wherein the foreign gene is introduced by crossing with a plant that comprises said foreign gene;

(4) the method according to (2), wherein a 5'-untranslated region of a gene encoding a seed storage protein is inserted between the foreign gene and the promoter that ensures the expression of the foreign gene in plant seeds;

(5) the method according to (4), wherein the 5'-untranslated region is a complete one;

(6) the method according to (4) or (5), wherein the 5'-untranslated region is that of a gene encoding a protein selected from the group consisting of glutelin, globulin, prolamin, and albumin;

(7) the method according to (6), wherein the 5'-untranslated region comprises the nucleotide sequence of SEQ ID NO: 1;

(8) the method according to any one of (1) to (7), wherein the defective seed storage protein in the plant is selected from the group consisting of glutelin, globulin, prolamin, and albumin;

(9) a transformed plant cell defective in endogenous seed storage protein into which a foreign gene has been introduced;

(10) a transformed plant cell defective in endogenous seed storage protein into which a vector comprising a foreign gene that is operatively connected downstream of a promoter that ensures the expression of the foreign gene in plant seeds is introduced;

(11) the transformed plant cell according to (10), wherein a 5'-untranslated region of a gene encoding a seed storage protein is inserted in the expression vector between the foreign gene and the promoter that ensures the expression of the foreign gene in plant seeds;

(12) the transformed plant cell according to (11), wherein the 5'-untranslated region is a complete one;

(13) the transformed plant cell according to (11) or (12) wherein the 5'-untranslated region is that of a gene encoding a protein selected from the group consisting of glutelin, globulin, prolamin, and albumin;

(14) the transformed plant cell according to (13), wherein the 5'-untranslated region comprises the nucleotide sequence of SEQ ID NO: 1;

(15) the transformed plant cell according to any one of (9) to (14), wherein the defective seed storage protein in the plant is a protein selected from the group consisting of glutelin, globulin, prolamin, and albumin;

(16) a transgenic plant comprising the transformed plant cell according to any one of (9) to (15);

(17) a vector comprising a promoter that ensures expression in plant seeds and a complete 5'-untranslated region of a gene encoding a seed storage protein that is connected to the promoter;

(18) the vector according to (17), wherein the 5'-untranslated region is that of a gene encoding a protein selected from the group consisting of glutelin, globulin, prolamin, and albumin;

(19) the vector according to (18), wherein the 5'-untranslated region of the glutelin gene comprises the nucleotide sequence of SEQ ID NO: 1;

(20) the vector according to any one of (17) to (19), wherein the promoter that ensures expression in plant seeds is a promoter of a gene encoding a protein selected from the group consisting of glutelin, globulin, prolamin, and albumin;

(21) the vector according to any one of (17) to (20), wherein a foreign gene is operatively connected downstream of the 5'-untranslated region;

(22) a transformed plant cell wherein the vector according to (21) is introduced;

(23) a transgenic plant comprising the transformed plant cell according to (22);

(24) a transgenic plant that is a progeny or clone of the transformed plant according to (16) or (23); and,

(25) a breeding material of the transgenic plant according to any one of (16), (23), and (24).

The present invention provides a method for accumulating high levels of a foreign gene product in plant seeds. This method is characterized by the use of a mutant plant that is defective in endogenous seed storage protein as a target for expressing the foreign gene. Herein, the term "defective" not only comprises a complete deletion but also a partial deletion. In such plants, the amount of free amino acids that are available for protein translation is considered to be larger than in normal plants; this enables efficient accumulation of foreign gene translation product in seeds. There is no particular limitation on the defective seed storage protein in plants; the invention includes, for example, glutelin, globulin, prolamin, and albumin.

Plants defective in these proteins may be selected from seeds of plants treated by irradiation, such as with γ-ray, or with a mutation-inducing agent, such as EMS and MNU. Mutant plants may be selected by the seed bisection method. Specifically, a seed is cracked in two, and protein is extracted from the endosperm to select seeds with the desired phenotype. Progenies can be obtained from the embryos corresponding to the selected endosperm with the desired phenotype.

Alternatively, plants with a reduced accumulation level of seed storage protein may. be generated through co-suppression or the antisense method. For co-suppression, a part of a gene encoding a seed storage protein to be decreased is modified and introduced into plants. In this way, the expressions of genes having a homology higher thab a certain value to the modified gene can be suppressed (for example, in the above-mentioned LGC-1 mutant, originated from plants irradiated with γ-ray, co-suppression is suggested to have occurred, due to the mutation of the glutelin α1 subunit gene). On the other hand, in the antisense method, a DNA encoding an antisense RNA that is complementary to the transcription product of a gene to be reduced is introduced into plants.

According to the present invention, known mutants of rice that lack major storage protein, such as LGC-1 and α123, may be also used.

Any gene suitable for expression in the seeds of plants may be used as a foreign gene. For example, crops with high additional values, rich in nutrition, having excellent features for processing, and/or functioning to maintain and improve health by decreasing the level of blood cholesterol in human, can be produced using soybean glycinin as the foreign gene (Japanese Patent No. 3030339). Alternatively, a vaccine gene for passive immune therapy, a modified glutelin gene wherein a physiologically active peptide is integrated into its variable region, or a useful enzyme gene can be introduced into rice to produce rice with high additional value.

In order to express a foreign gene in plant seeds, a vector comprising the foreign gene operatively connected downstream of a promoter that ensures the expression in plant seeds may be favorably used. Herein, the phrase "operatively connected" means that the foreign gene and the promoter are connected so to express the foreign gene in response to the activation of the promoter.

For example, for expression in rice seeds, the glutelin gene promoter (Takaiwa, F. et al., Plant Mol. Biol. 17: 875-885 (1991)) may be used as the foreign gene expression promoter. When expressed in bean plants, such as string bean, horse bean, and pea; or oilseed plants, such as peanut, sesame, rapeseed, cottonseed, sunflower, and safflower, the glycinin gene promoter or the promoter of a major storage protein gene of respective plants can be used. For example, the phaseolin gene promoter (Murai, N. et al., Science 222: 476-482 (1983)) and the cruciferin gene promoter (Rodin, J. et al., Plant Mol. Biol. 20: 559-563 (1992)) may be used for string bean and rapeseed, respectively. The above promoters are just given as examples, and promoters for constitutive expression, such as the 35S promoter, may be also used.

It is preferable to insert a 5'-untranslated region of a gene encoding a seed storage protein between the promoter and the foreign gene within a vector for efficient accumulation of the foreign gene product in plant seeds. Examples of such a 5'-untranslated region include those of genes encoding glutelin (X54313,*Oryza sativa* GluA-3 gene for glutelin, gi|20207|emb|X54313.1|OSGLUA3[20207]; X54314, *O. sativa* GluB-1 gene for glutelin, gi|20209|emb|X54314.1|OSGLUB1[20209]), globulin (X62091, LOW MOLECULAR WEIGHT GLOBULIN, gi|5777591|emb|X62091.1|OSLMWG[5777591]), prolamin (D11385, *Oryza sativa* mRNA for prolamin, complete cds, gi|218186|dbj|D11385.1|RICPLM[218186]) and albumin (D11431, Rice RA17 gene for allergenic protein, complete cds, gi|218194|dbj|D11431.1|RICRA17[218194]; D11432, Rice RA14 gene for allergenic protein, complete cds, gi|218192|dbj|D11432. 1|RICRA14[218192]) Especially preferred are 5'-untranslated regions in a complete form. In the present invention, chimeric 5'-untranslated regions derived from genes encoding two different seed storage proteins may be also used. The complete 5'-untranslated region of the GluB-1 gene is shown in SEQ ID NO: 1.

A vector wherein a 5'-untranslated region is inserted downstream of a promoter that ensures the expression in plant seeds and a vector wherein a foreign gene is further inserted may be constructed using gene manipulation techniques known to those skilled in the art.

Considering the essence of the present invention, there is no limitation on plants to derive a plant cell for introducing a vector, so long as it is a seed plant. For example, the plants encompassed by the present invention include grains, such as rice, barley, triticum, rye, and maize; beans, such as string bean, horse bean, and pea; and oilseed plants, such as peanut, sesame, rapeseed, cottonseed, sunflower, and safflower; and so on.

The forms of plant cell contemplated for introduction of a vector in the present invention include all kinds of forms that can be regenerated into a plant. For example, the forms encompassed by the present invention include cultured cells, protoplast, shoot primordium, polyblasts, hairy roots, and callus, but are not limited thereto. Cells in a plant are also included in the plant cell of the present invention.

Methods known to those skilled in the art may be used to introduce a vector into plant cells. For example, such methods include indirect transduction, using *Agrobacterium tumefaciens* or *Agrobacterium rhizogenes* (Hiei, Y. et al., Plant J. 6: 271-282 (1994); Takaiwa, F. et al., Plant Sci. 111: 39-49 (1995)); and direct transduction, represented by the electroporation method (Tada, Y. et al., Theor. Appl. Genet. 80: 475 (1990)), the polyethylene glycol method (Datta, S. K. et al., Plant Mol. Biol. 20: 619-629 (1992)) and the particle bombardment method (Christou, P. et al., Plant J. 2: 275-281 (1992); Fromm, M. E., Bio/Technology 8: 833-839 (1990)).

Plants can be produced by regenerating a transformed plant cell. The method for regeneration may differ depending on the type of the plant. However, representative methods include the method of Fujimura et al. (Fujimura, T. et al., Plant Tissue Culture Lett. 2: 74 (1995)), the method of Armstrong et al. (Armstrong, C. L. and Phillips R. L., Crop Sci. 28: 363-369 (1988)), and the method of Radke et al. (Radke, S. E. et al., Theor. Appl. Genet. 75: 685-694 (1988)) for rice, maize, and rapeseed, respectively.

In addition to the above methods, crossing may be used to introduce a foreign gene into a plant defective in endogenous seed storage protein. For example, first, a plant harboring the foreign gene within the genome is generated by introducing the above-mentioned vector. Then, the plant is crossed with a plant that is defective in. endogenous seed storage protein to introduce a foreign gene into the endogenous seed storage protein defective plant.

Once a transgenic plant, wherein a foreign gene is introduced into the genome, is obtained, progeny of the plant may be obtained by sexual reproduction. Alternatively, propagative materials (such as seeds, strain, callus, and protoplast) may be obtained from the plant and progeny or clones thereof as the starting material to generate the plant in large quantities. The transgenic plants of the present invention can accumulate high levels of a foreign gene product in seeds by expressing the foreign gene. Accordingly, food value, the feature for process, health improving function, and such of a seed may be effectively modified depending on the characteristic of the foreign gene product selected for accumulation within the seed. Furthermore, pharmaceutical products and industrial materials may be efficiently manufactured by accumulating antibody or enzyme in seeds.

BEST MODE FOR CARRYING OUT THE INVENTION

Herein below, the present invention will be specifically described using Examples, but it is not to be construed as being limited thereto.

EXAMPLE 1

Figure 1:
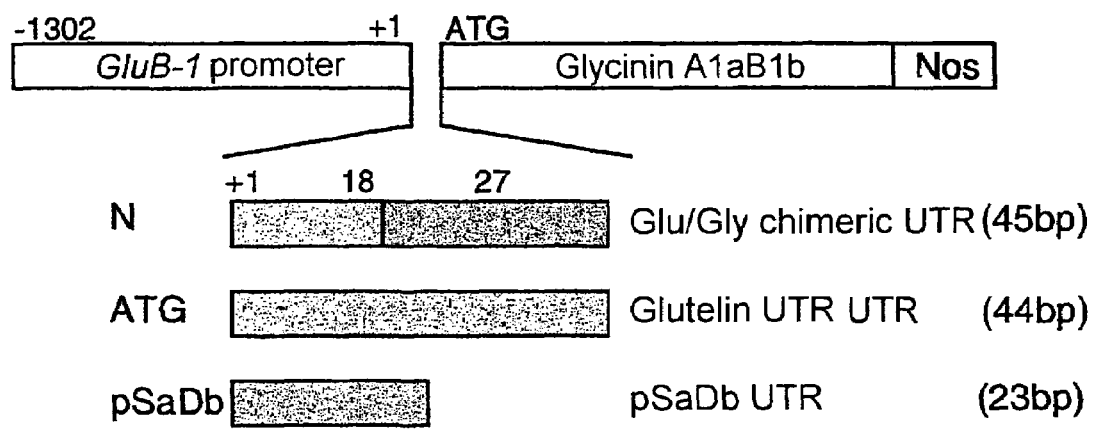
FIG. 1 shows the constructs used for examining the effect of a 5'-untranslated region (UTR).

Construction of Soybean Glycinin Expression Vector Using an Improved Promoter, and Generation of Rice Plant Expressing Soybean Glycinin (1) Construction of Chimeric Gene and Gene Transfer A cDNA encoding glycinin (A1aB1b) was ligated to GluB-1 gene promoter. Between the cDNA and the promoter, a chimeric sequence (45 bp) of the untranslated regions of glutelin (+1 to 18) and glycinin (−27 to ATG) was inserted for N, and the complete 5'-untranslated region (44 bp) of GluB-1 gene for ATG (FIG. 1). As a control, an expression vector inserted with the 5'-untranslated region of pSaDb, translation enhancer sequence of a tobacco photosynthesis gene, was constructed. These plasmids comprising these chimeric genes were introduced. into rice (Oryza sativa cv Kitaake) using the Agrobacterium method (Goto, F. et al., Nat. Biotechnol. 17: 282-286 (1999)).

11-5 was selected from rice (Oryza sativa cv Matsuyama-mii) to which a chimeric gene wherein a cDNA encoding glycinin (A1aB1b) was connected to GluB-1 gene promoter (−1302 to +18) has been transferred by the electroporation method.

Figure 2:
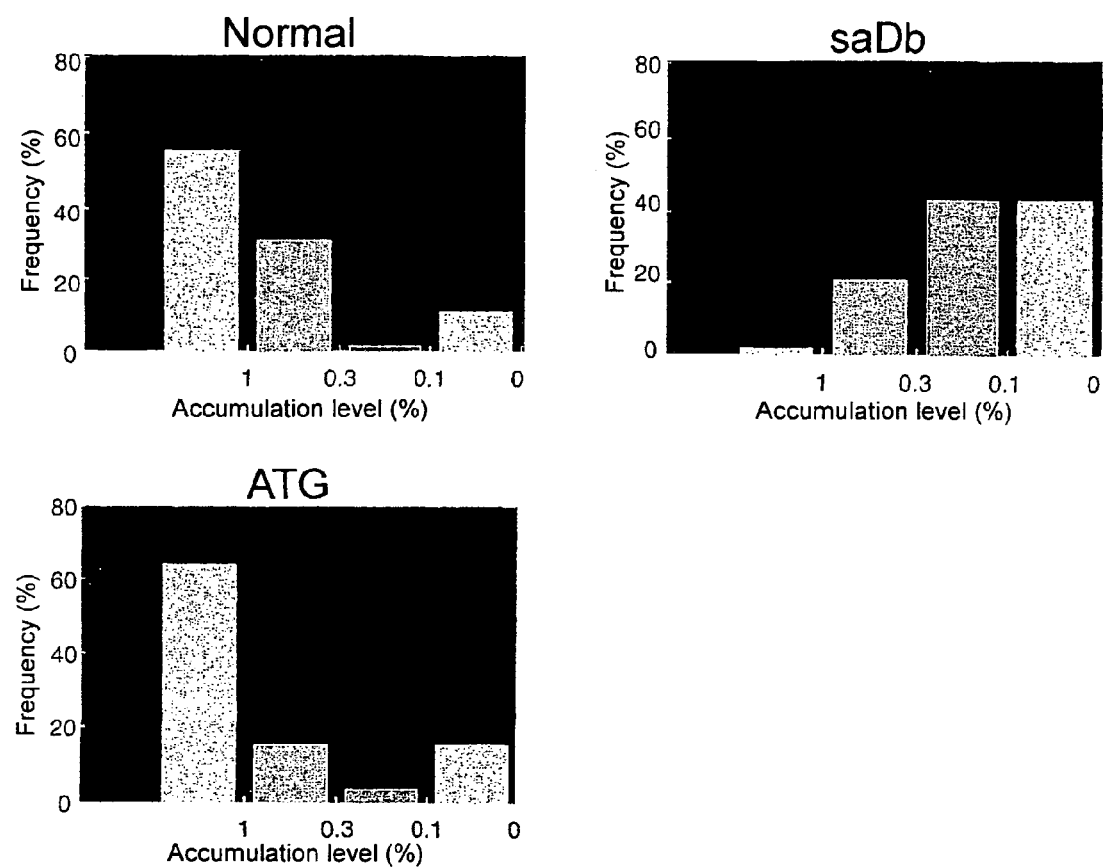
FIG. 2 shows the result of comparison of the measured levels of glycinin accumulation in the plants transformed with the constructs comprising the 5'-untranslated region of FIG. 1.

(2) Effect of 5'-Untranslated Region of GluB-1 Gene on the Expression of Foreign Gene in Plant Seeds A gene was introduced into plants by the Agrobacterium method, and seeds (T1) of the obtained plants were analyzed for the protein level. By comparing N, pSaDb, and ATG, it was revealed that the frequency of occurrence of plants accumulating high levels of glycinin is higher in the order of ATG>N>pSaDb (FIG. 2).

Next, strains having the highest expression level were selected from each of the N and ATG transgenic strains that accumulated high levels of glycinin, and were self-fertilized to screen for a homozygote. Then, the levels of mRNA and protein in homozygotes were analyzed as follows. For RNA analysis, first, RNA was extracted by the SDS-phenol method. 12 immature seeds approximately 15 days after flowering were frozen with liquid nitrogen, and pounded in a mortar into fine powder. Buffer (0.1 M Tris-HCl (pH 9.0), 1% SDS, 0.1 M NaCl, 5 mM EDTA) and phenol-chloroform-isoamyl alcohol (25:24:1) were mixed thereto, and total nucleic acid was extracted. The sample was centrifuged to recover the supernatant, and was extracted again with phenol-chloroform-isoamyl alcohol (25:24:1). Then the total nucleic acid was collected by ethanol precipitation, and redissolved in distilled water. Then, RNA was precipitated in 2M LiCl, and was recovered by centrifugation as the sample. The RNA was electrophoresed on a 1.2% agarose gel, and was transferred onto a nylon membrane. The prepared membrane was hybridized with $^{32}$P-labeled glycinin (A1aB1b) cDNA at 42° C. in 50% (v/v) formamide, 6× SSC, 0.5% (w/v) SDS, and 5× Denhardt's solution. Then, the membrane was washed three times in 2× SSC, 0.1% SDS solution at room temperature, and once in 0.1× SSC, 0.1% SDS solution at 55° C. for 20 min. For protein analysis, total protein was extracted using 250 µl of extraction buffer (62.5 mM Tris-HCl (pH 6.8) containing 10% (v/v) glycerol, 0.25% (w/v) SDS, and 5% 2-mercaptoethanol) per 10 mg of mature seed. The extracted protein was treated at 100° C. for 5 min, and then was subjected to SDS-PAGE. SDS-PAGE was performed using a 15% (w/v) polyacrylamide gel (acrylamide: N,N'-methylenebisacrylamide=30:0.8).

Figure 3:
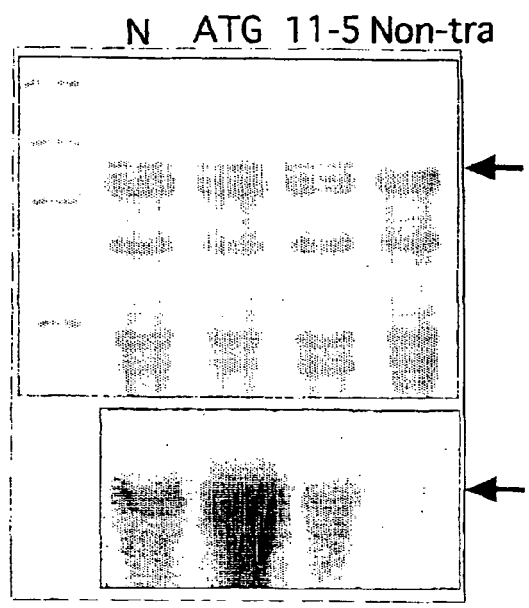
FIG. 3 shows the accumulation and expression of soybean glycinin in transgenic rice seeds. (A) shows photographs demonstrating the results of SDS-PAGE analysis (top) and Northern blot analysis (bottom). (B) shows a chart wherein the results in (A) are quantified and compared. N indicates the plant comprising a chimeric sequence of the untranslated regions of the glutelin and glycinin; ATG that comprising the complete 5'-untranslated region of the glutelin gene; 11-5 a conventional glycinin gene transductant; and Non-tra a non-transgenic plant.

As a result, the expression levels of A1aB1b in N and ATG were found to be 1.43 and 6.56 times, respectively, as much as that in 11-5 (FIG. 3). According to a comparison of the protein accumulation level by separating the acidic subunits of glycinin by SDS-PAGE, the accumulation level of A1aB1b in N and ATG were 1.40 and 1.62 times, respectively, as much as that in 11-5 (FIG. 3). These results show that the insertion of a 5'-untranslated region, specifically the complete 5'-untranslated region of the GluB-1 gene, between the GluB-1 gene promoter and a cDNA encoding glycinin (A1aB1b) is effective to improve the expression level of a foreign gene.

EXAMPLE 2

Development of a Technique for Accumulating Foreign Gene Product at a High Level Using Mutants 11-5 (Momma, K. et al., Biosci. Biotechnol. Biochem. 63: 314-318 (1999)) was crossed with either LGC-1 (Iida, S. et al., Theor. Appl. Genet. 87: 374-378 (1993)) or α123 (Iida, S. et al., Theor. Appl. Genet. 94: 177-183 (1997)), and their F1 seeds were collected. The seeds were cracked in two (the seed bisection method), and endosperm was used for protein extraction and analysis by SDS-PAGE. Based on the result of SDS-PAGE analysis, seeds showing an intense band corresponding to glycinin and a weak band for the acidic subunit of glutelin were selected. By repeating such selection, plants that are homogenous in all phenotypes were obtained.

Figure 4:
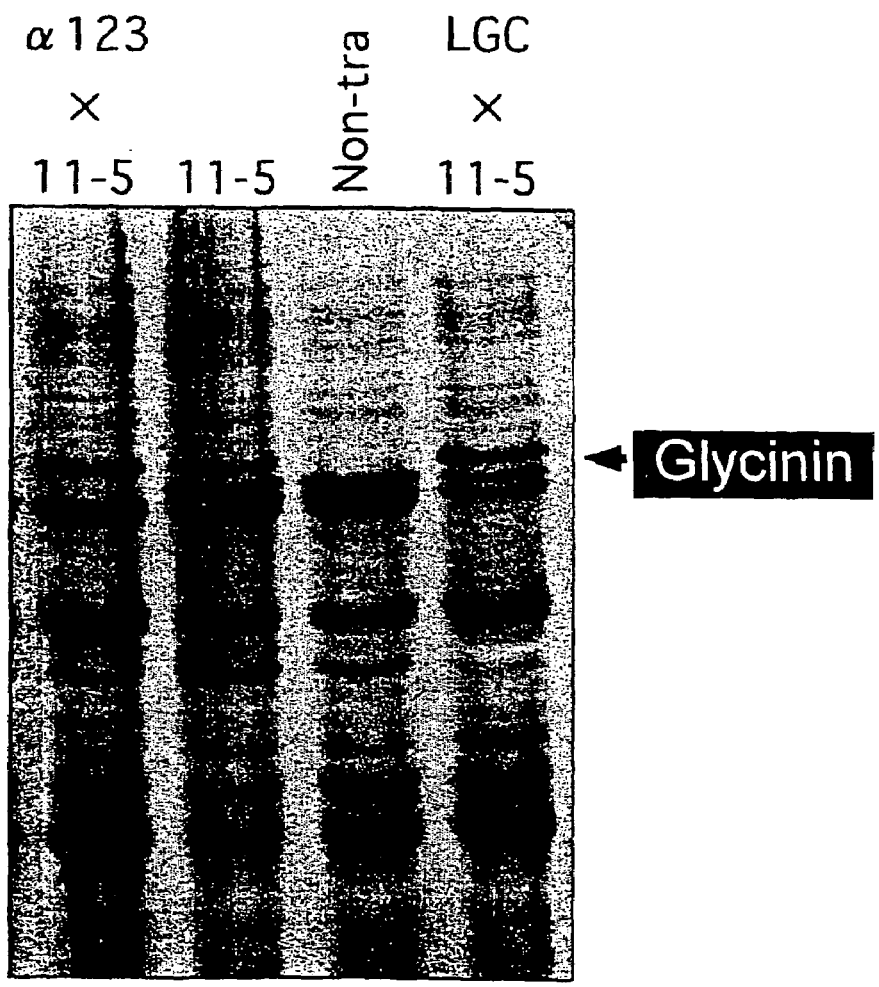
FIG. 4 is a photograph depicting the effect of glutelin deficient phenotype on foreign gene product accumulation by SDS-PAGE analysis of the endosperm proteins. 11-5 indicates transgenic Matsuyama-mii comprising the glycinin (A1aB1b) gene; LGC indicates LGC-1; and Non-tra the non-transgenic plant.

The endosperm protein in LGCx11-5 and α123x11-5 were analyzed by SDS-PAGE (FIG. 4). As a result, LGCx11-5 showed the phenotype of LGC-1 wherein the band for all 37 to 39 kDa acidic subunits of glutelin became weak (the total amount of glutelin was decreased to approximately one third). In contrast, the band corresponding to the acidic subunit of the transgenic product glycinin was significantly thickened (1.4 fold) compared to the glycinin transductant 11-5. On the other hand, α123x11-5 were defective in glutelin acidic subunits α1, α2, or α3, and showed the same phenotype as α123. In α123x11-5, the band corresponding to the acidic subunits of the transgenic product glycinin was significantly thickened (1.7 fold) compared to the glycinin transductant 11-5.

Next, the amount of accumulated transgenic product, glycinin A1aB1b, was quantified. Specifically, total proteins extracted from seeds were spotted on nitro cellulose membrane, and were subjected to immunoblotting using anti-glycinin (A1aB1b) antibody. As a result, the band of the acidic subunit of transgenic product glycinin was significantly thickened in seeds of plants that were crossed with LGC-1. Furthermore, a similar result was obtained for those crossed with α123. These results revealed that the addition of the phenotype defective in seed storage protein to a line that accumulate foreign gene product in the endosperm of seeds enable accumulation of the foreign gene product at a high level.

Industrial Applicability

The present invention provides a method for accumulating high levels of a foreign gene product in plant seeds. The method of the present invention may serve as an important fundamental technique for developing useful agricultural products and foods.

The invention claimed is:

1. A method for accumulating a foreign gene product in a plant seed comprising the steps of:
   (a) providing a mutant plant that produces seeds that lack or have a reduced level of endogenous glutelin as compared to a wild-type plant of the same species;
   (b) introducing a vector comprising a foreign gene into the provided plant of step (a), the vector comprising a sequence encoding a foreign gene product operably connected downstream of a rice GluB-1 gene promoter and the complete 5'-untranslated region of a the rice GluB-1 gene comprising the nucleotide sequence of SEQ ID NO:1 inserted between the rice GluB-1 gene promoter and the sequence encoding the foreign gene product; and
   (c) expressing the foreign gene to produce the foreign gene product in the plant seed of the plant obtained in step (b), wherein the plant seed lacks or has a reduced level of endogenous glutelin as compared to a wild-type plant of the same species.

2. The method according to claim 1, wherein the vector is introduced by crossing the provided mutant plant of step (a) with a plant that expresses the foreign gene in its seeds.

3. A transgenic plant, derived from a mutant plant having seeds that lack or have a reduced level of endogenous glutelin as compared to a non-mutant plant of the same species so that said transgenic plant produces seeds that lack or have a reduced level of endogenous glutelin as compared to a non-mutant plant of the same species, said transgenic plant comprising a vector that comprises a foreign gene, the vector comprising a sequence encoding a foreign gene product operably connected downstream of a rice GluB-1 gene promoter, and the complete 5'-untranslated region of the rice GluB-1 gene comprising the nucleotide sequence of SEQ ID NO: 1 inserted between the rice GluB-1 gene promoter and the sequence encoding the foreign gene product, and wherein the transgenic plant produces a higher level of the foreign gene product in its seeds compared to that in a wild-type plant that expresses the foreign gene.

4. An isolated plant cell of the transgenic plant according to claim 3, into which the vector comprising the foreign gene has been introduced.

5. The method according to claim 1, wherein the plant is a grain plant, bean plant, or oilseed plant.

6. The method according to claim 1, wherein the plant is selected from the group consisting of rice, barley, triticum, rye, maize, string bean, horse bean, soybean, pea, peanut, sesame, rapeseed, cottonseed, sunflower, and safflower.

7. The transgenic plant according to claim 3, wherein the plant is a grain plant, bean plant, or oilseed plant.

8. The transgenic plant according to claim 3, wherein the plant is selected from the group consisting of rice, barley, triticum, rye, maize, string bean, horse bean, soybean, pea, peanut, sesame, rapeseed, cottonseed, sunflower, and safflower.

9. A transgenic plant, prepared by introducing a vector comprising a foreign gene into a mutant plant having seeds that lack or have a reduced level of endogenous glutelin as compared to a wild-type plant of the same species, said foreign gene comprising a sequence encoding a foreign gene product operably connected downstream of a rice GluB-1 gene promoter, and the complete 5'-untranslated region of the rice GluB-1 gene comprising the nucleotide sequence of SEQ ID NO: 1 inserted between the rice GluB-1 gene promoter and the sequence encoding the foreign gene product, wherein the transgenic plant produces a higher level of the foreign gene product in its seeds compared to that in a wild-type plant that expresses the foreign gene and wherein the transgenic plant has seeds that lack or have a reduced level of endogenous glutelin compared to a wild-type plant of the same species.

* * * * *

SEQUENCE LISTING

<160> NUMBER OF SEQ ID NOS: 1

<210> SEQ ID NO 1
<211> LENGTH: 44
<212> TYPE: DNA
<213> ORGANISM: Oryza sativa

<400> SEQUENCE: 1
tcacatcaat tagcttaagt ttccataagc aagtacaaat agct                44